United States Patent [19]

Kelman

[11] Patent Number: 5,123,906
[45] Date of Patent: Jun. 23, 1992

[54] SURGICAL TOROIDAL SNARE

[76] Inventor: Charles D. Kelman, 721 Fifth Ave., New York, N.Y. 10022

[21] Appl. No.: 718,029

[22] Filed: Jun. 20, 1991

[51] Int. Cl.$^5$ .............................................. A61F 9/00
[52] U.S. Cl. .................................. 606/107; 606/113; 623/6
[58] Field of Search ...................... 606/107, 110–114, 606/127–128; 623/6

[56] References Cited

U.S. PATENT DOCUMENTS

| | | | |
|---|---|---|---|
| 4,214,585 | 7/1980 | Bailey, Jr. | 606/107 |
| 4,429,421 | 2/1984 | Levy | 606/107 |
| 4,530,117 | 7/1985 | Kelman | 606/107 |
| 4,538,611 | 9/1985 | Kelman | 606/107 |
| 4,699,140 | 10/1987 | Holmes et al. | 606/107 |
| 4,917,680 | 4/1990 | Poley | 623/6 |

*Primary Examiner*—Stephen C. Pellegrino
*Assistant Examiner*—Glenn K. Dawson
*Attorney, Agent, or Firm*—Darby & Darby

[57] ABSTRACT

A surgical instrument for seating an intraocular lens in the posterior capsule of an eye in place of a removed cataracted natural lens includes a longitudinally extending shank and a band attached to the shank and forming a closed loop. The loop extends outwardly of the S-shaped tip portion of the shank for holding the intraocular lens in a plane which is generally parallel to and laterally displaced from the longitudinal axis of the shank. The band has a first end connected with the shank for movement therewith, and a second end connected to a support member located in the shank for movement therewith and relative thereto. The member, when displaced in the shank bore relative to the shank, tears the band, breaking the loop. Thereby, upon withdrawal of the instrument from the eye, the band is withdrawn together with the instrument without disturbing the seating of the intraocular lens in the posterior capsule.

12 Claims, 2 Drawing Sheets

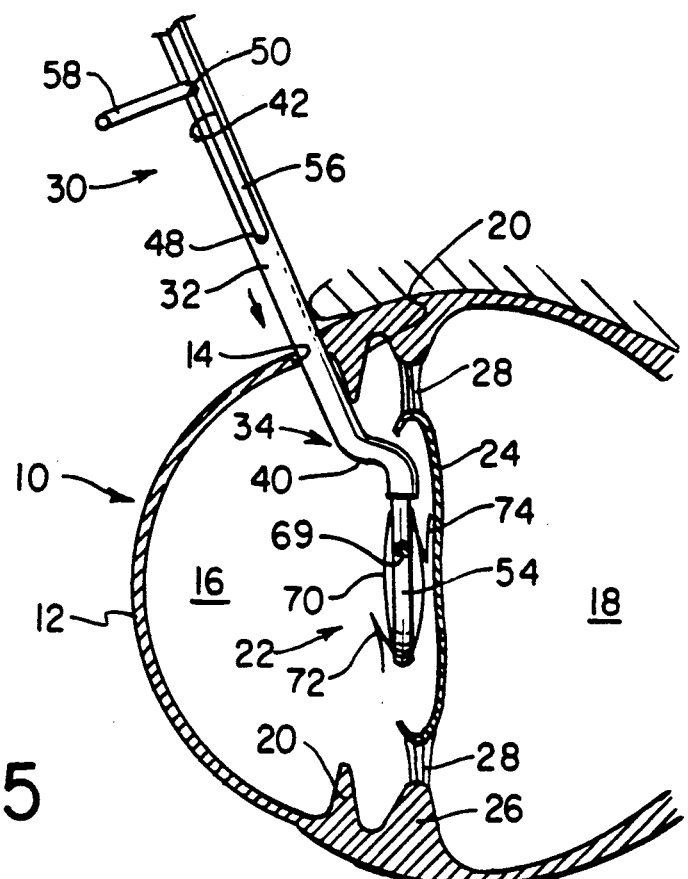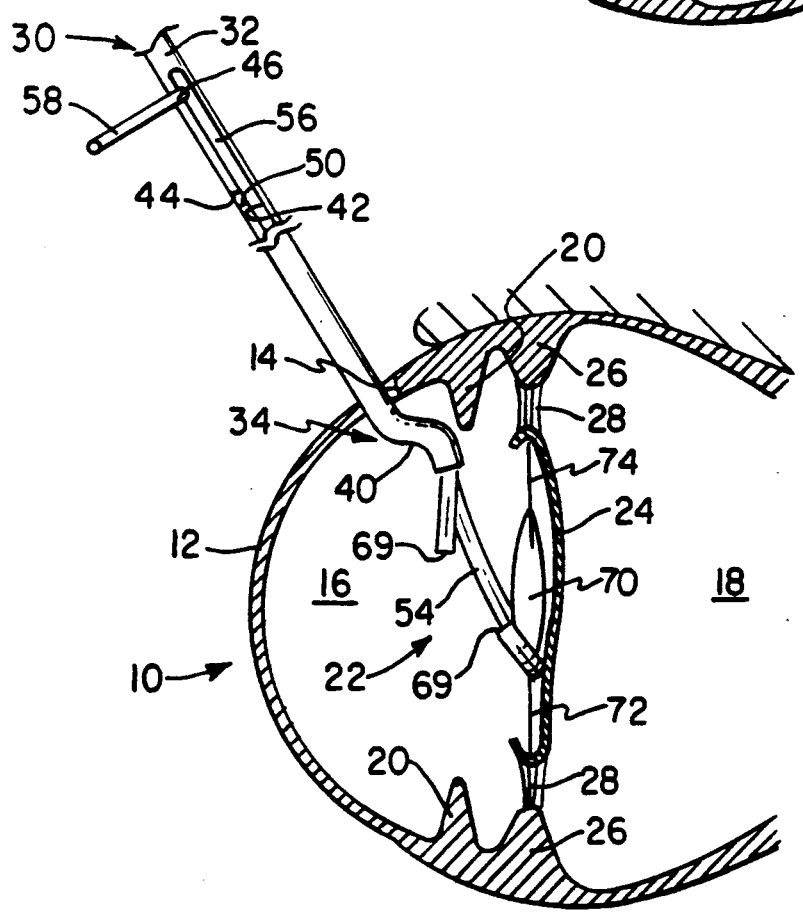

SURGICAL TOROIDAL SNARE

BACKGROUND OF THE INVENTION

1. Field of the Invention

The present invention relates to a surgical instrument for seating an intraocular lens in a posterior chamber of an eye in place of a cataracted natural lens removed during a cataract operation. In particular, the present invention relates to a surgical snare for seating an intraocular lens in a posterior capsule that remains after extracapsular removal of a cataracted natural lens.

2. Description of the Pertinent Art

A surgical snare for cutting a cataracted lens of a human eye is disclosed in my U.S. Pat. No. 4,538,611. The surgical snare cutter disclosed therein comprises a loop which is adapted to snare the natural lens of an eye, crosswise of such lens, i.e., along a diameter thereof, and to cut the same upon movement of the loop member, which is displaceable within the bore of the shank of the instrument, to its retracted condition.

A surgical instrument for seating an intraocular lens in a posterior chamber of an eye is disclosed in my U.S. Patent No. 4,530,117. Generally, an intraocular lens used to replace a cataracted natural lens includes a lens and a pair of opposed position fixation members called haptics for retaining the intraocular lens in the posterior chamber. U.S. Pat. No. 4,530,117 disclosed an instrument for seating an intraocular lens of the type described, in the posterior chamber. The instrument has a longitudinal shank portion and a hooked end portion. The hooked end portion has a tip portion adapted to engage the upper haptic of the lens for displacing the upper haptic toward the lower haptic during the insertion of the lens through the pupil of the eye. After the lower haptic of the lens is seated in the lower portion of the posterior capsule, the instrument is operated to move the upper haptic through the pupil into the posterior capsule and let the upper haptic expand to its undeformed condition in the posterior capsule. While the above-described hooked instrument substantially simplified the lens seating procedure, it, nevertheless, continued to be a difficult procedure to properly seat both haptics in the capsular bag.

SUMMARY OF THE INVENTION

The principal object of the invention is to provide a new and improved surgical instrument that avoids the disadvantages of the prior art instruments.

It is another object of the invention to provide a new and improved surgical instrument that can both hold the lens and seat it in the posterior capsule of an eye.

It is a further object of the invention to provide a new and improved surgical instrument that is easily disengaged from the lens once the lens is seated in the posterior capsule.

These and other objects of the invention that will become apparent hereafter, are achieved by providing a surgical snare for holding the intraocular lens during insertion into the eye and for seating it in the posterior capsule. The snare according to the invention comprises a hollow longitudinal shank with a tip portion from which a toroidal band loop extends outwardly. The band loop has a size adapted to accommodate the lens and the deformed opposed haptics of the lens. In one embodiment, one end of the band loop is fixedly secured to the shank, preferably at the tip portion thereof. The other end of the band loop extends into the tip portion mouth and is free to be pulled further into the mouth in order to close, i.e., reduce the size of, the loop for peripherally embracing an intraocular lens therein. The length of the band is so selected that it will, in the contracted condition of the loop, fit snugly about a 6 mm diameter lens. The other end extending into the top portion is, in this embodiment, secured to a member movable within the shank bore between forward and retracted positions. The band is preferably a thin, very flexible plastic and, in accordance with an aspect of my invention, may have a weakened portion at one point in its periphery. The movable member has, in the shank, a forward position in which the loop is of a size facilitating loosely placing an intraocular lens therein, an intermediate position in which the loop snugly fits around the periphery of the lens, and a rearward position. With the movable member in the intermediate position, the tip of the instrument, with the loop-held lens in front, is inserted into the eye. The tip is generally S-shaped so that the shank will clear the iris while the loop-held lens is positioned parallel to and adjacent the posterior wall of the posterior capsule. When the lens is seated in the posterior capsule, and the snare has to be removed, the movable member is retracted toward its rearward position in the shank body, tearing the weakened portion of the band to release it from around the lens, and the band is removed when the instrument is withdrawn. The tearing is accomplished against the slight opposing pressure of the lens positioned in the loop.

In another embodiment, the band has a hole at its end secured to the movable member through which a metal or nylon wire extends, the wire being connected to a front end of the movable member within the shank bore. Upon movement of the member to its rearward position, the wire cuts the band, releasing it from its connection with the movable member. In both embodiments, the S-shape of the tip of the instrument is proportioned to allow the tip to accommodate the iris of the eye by extending around the iris.

Providing a surgical snare with a breakable lens holding loop according to the invention substantially facilitates seating of an intraocular lens in the posterior chamber of an eye and withdrawal of the snare from the eye without disturbing the seating of the lens.

The present invention, both as to its construction and as to its mode of operation together with additional objects and advantages thereof, will be best understood from the following detailed description of the preferred embodiments when read with reference to the accompanying drawings.

BRIEF DESCRIPTION OF THE DRAWINGS

FIG. 4 is an enlarged fragmented sectional view of a human eye with the surgical snare according to the invention shown holding an intraocular lens just prior to withdrawing of the band from around the lens;

FIG. 5 is an enlarged fragmented sectional view of a human eye with a surgical snare according to the invention in its partially withdrawn position and with the intraocular lens partially seated;

DETAILED DESCRIPTION OF THE PREFERRED EMBODIMENT

Figure 1:
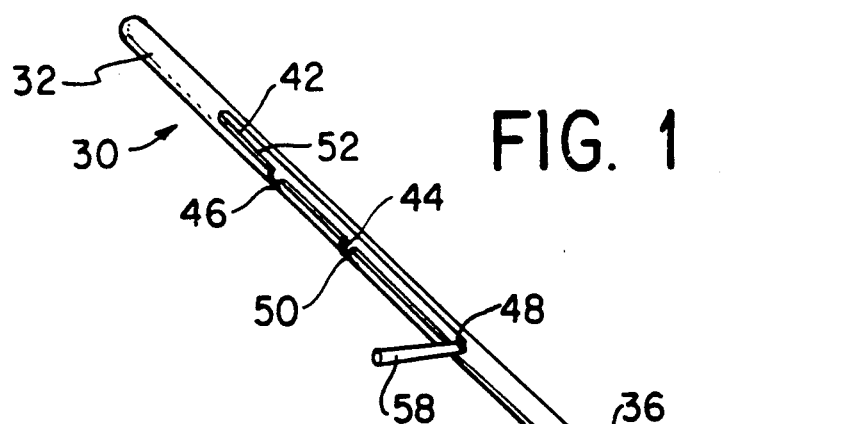
FIG. 1 is a perspective view of a surgical snare according to the invention.

In the drawings, FIGS. 4 and 5 show a fragmented sectional view of a human eye 10 with some portions omitted for the sake of clarity. The eye 10 has a cornea 12 in which a surgeon makes an incision opening 14 for removing the cataracted natural lens and inserting an intraocular lens. The eye 10 has anterior and posterior chambers 16 and 18 defined by the position of an iris 20. The iris defines a central opening or pupil 22. After extracapsulary removal of the cataracted natural lens, the posterior capsule 24 and peripheral portion of the anterior capsule remain intact. The capsule 24 is normally connected to the ciliary body 26 of the eye by zonulas 28 at the opposed ends of the capsule 24.

Figure 2:
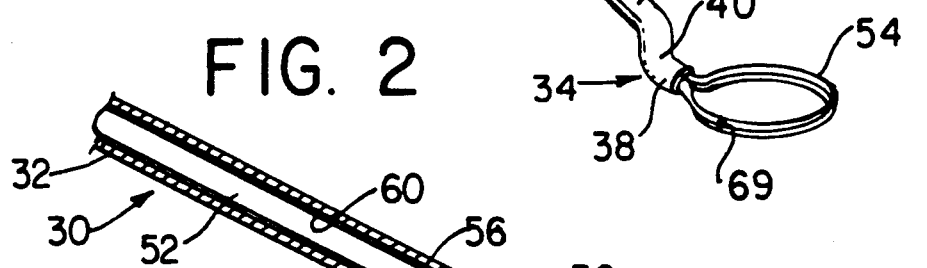
FIG. 2 is a partial longitudinal cross-sectional view of a surgical snare according to a first embodiment of the invention.

One embodiment of the surgical snare 30, in accordance with my invention, for seating an intraocular lens in the posterior capsule 24 is shown in detail in FIGS. 1 and 2 and, as shown, comprises a longitudinal hollow shank 32 having a preferably substantially S-shaped tip portion 34. The tip portion 34 consists of two arms 36 and 38 connected by a transition portion 40 for accommodating the iris. As shown in FIG. 1, the shank has a first longitudinal slot 42, a second transverse slot 44, and a third transverse slot 46. The axial planes of slots 44 and 46 intersect at an angle of 90° at the axial plane of the slot 42. The slots 42,44 have respective front surfaces 48 and 50 which define, respectively, forward and intermediate positions of a movable support member 52 that provides for securing a band loop 54 in the mouth of the tip portion 34. The member 52 has an axially extending part or plunger 56 and a projection 58 extending transverse to the axis of the plunger 56. In the forward position of the movable member 52 with the projection 58 against surface 48, the size of the loop is such that an intraocular lens with haptics can be easily positioned therein. In the intermediate position of the movable member 52 with projection 58 against surface 50, the size of the band loop 54 is reduced so that it snugly fits around the periphery of the lens.

The plunger 56 extends into a bore 60 of the shank 32 and is displaceable therein. The projection 58 is displaceable in the slot 42 and projects through the transverse slots 44 or 46 for engagement by a surgeon. The plunger 56 of the movable member 52 may represent a friction plunger that presses a free end 62 of the band loop 54 radially against the interior wall of the tip portion 34. The other end 64 of the band loop 54 is generally fixedly secured to the interior wall of the shank 32.

Figure 3:
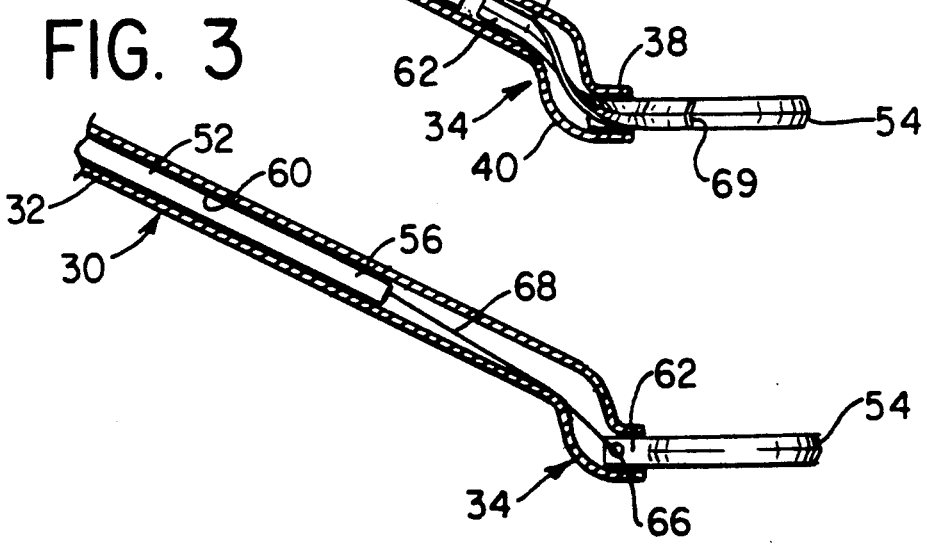
FIG. 3 is a partial longitudinal cross-sectional view of a surgical snare according to a second embodiment of the invention.

In another embodiment shown in FIG. 3, the free end 62 of the band loop 54 has a hole 66, while the other end 64, not seen in FIG. 3, is again fixedly attached to the interior wall of the shank 32. The plunger 56 in this embodiment is much shorter and has a wire 68 connected at its one end to the front face of the plunger 56. The other end of the wire engages the hole 66 at the end of the band loop 54.

The band, in the embodiment shown in FIG. 1, has a weakened portion, such as a smaller cross-section part 69. Alternatively, the weakened portion may be provided by the hole 66.

Figure 6:
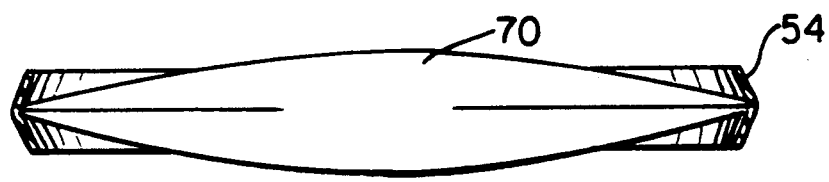
FIG. 6 is an enlarged transverse sectional view of the toroidal band loop with the lens held therein.

The band forming the loop 54 is preferably 0.5 mm wide and is preformed into a shape that curves with a radius of about 0.25 mm transversely to its longitudinal direction forming thus essentially a toroidal loop at the tip of the instrument. The cross-section of the loop 54, which is substantially C-shaped, is shown in FIG. 6. The band loop 54 holds a lens 70 with opposed deformed haptics 72 and 74. The band is made of polyethylene, nylon, mylar or similar thin flexible material compatible with the interior of the human eye.

In operation, when the member 52 is in its forward position with the projection 58 abutting the front face 48 of the slot 42, the lens is placed into the oversize loop 54. Thereafter, the surgeon retracts the member 52 to its intermediate position, in which the projection 58 abuts the front face 50 of the second slot 44, to contract the band loop so that it snugly holds the lens, and pivots the projection 58 by 90° into the slot 44. Then, the tip portion 34 with the contracted band loop 54 with the lens therein is inserted through the incision 14 in the eye cornea. Further insertion of the S-shaped tip portion of the instrument through the incision allows the surgeon to position the loop inside the posterior capsule in a generally flat position with respect to the posterior wall of the capsule. This flat positioning is possible as a result of the S-shape of the tip portion 34. Thus, the offset of the axis of the mouth of the tip portion with respect to the axis of the handle of the instrument, an offset of approximately 1½ mm, compensates for the spacing along the optical axis between the iris and the interior of the posterior capsule. Once the loop-encircled lens is in this flat position within the capsule, the surgeon, breaks the band forming the loop at its weakened portion. This permits the surgeon to withdraw the tip portion of the instrument, together with the now released band, from the eye. As the band is removed from around the lens, the haptics are able to expand into proper seating position within the capsule. The release of the band is effected by movement of the projection 58 rearward in the slot 42 until the projection 58 is received in the slot 46.

The instrument, according to the invention, can be made relatively cheaply and can, therefore, be disposable. Alternatively, the instrument may be in a more permanent form with a disposable, i.e., replaceable, band.

While the particular embodiments have been shown and described, various modification thereof will be apparent to those skilled in the art. Thus, one end of the band loop may be fixedly secured to the movable member and the other end of the band loop may be releasably attached to the interior wall of the shank. Therefore, it is not intended that the invention be limited to the disclosed embodiments or to the details thereof, and that departure may be made therefrom within the spirit and scope of the invention as defined in the appended claims.

What is claimed:

1. A surgical instrument for seating an intraocular lens in the posterior capsule of an eye and comprising:
   a longitudinally extending hollow shank having a body and a tip portion;
   flexible band means forming a loop extending forwardly of said tip portion for embracing the intraocular lens,
   said shank tip portion having a generally S-shape to allow said tip portion to curl around the iris of the eye to position said loop with the intraocular lens held therein inside the posterior capsule in a plane generally parallel to the posterior wall of the capsule; and support means displaceable within said hollow shank and connected to said band means;

said displaceable support means having in said hollow shank a forward position in which said loop is larger than the lens to be held therein, an intermediate position in which said loop snugly retains the lens, and a rearward position in which said band means releases the lens to enable withdrawal of said band means from the eye without disturbing the seating of the lens in the posterior capsule of the eye.

2. A surgical instrument as set forth in claim 1 wherein said loop formed by said band means has a toroidal cross-section.

3. A surgical instrument as set forth in claim 1 wherein said support means comprises a plunger displaceable in a bore of said shank and a projection extending transversely of a longitudinal extent of said shank and projecting through a slot in the shank body to be engaged by a surgeon, said plunger having a front end portion and a wire secured to said front end portion, extending in said bore and engaging said band means.

4. A surgical instrument as set forth in claim 1 wherein said support means comprises an L-shaped member having one leg thereof displaceable in said shank and the other leg thereof extending transversely of a longitudinal extent of the shank and projecting through a slot in the shank body to be engaged by a surgeon, said one leg having a front end portion frictionally engaging said band means.

5. A surgical instrument as set forth in claim 1 wherein said band means has a weakened portion and said support means, upon displacement thereof to the rearward position thereof, severing said band means at said weakened portion from its connection with a remaining portion of said band means.

6. A surgical instrument as set forth in claim 1 wherein said band means comprises a flexible band having a substantially C-shaped transverse cross-section for embracing the periphery of the intraocular lens.

7. A surgical instrument as set forth in claim 1 wherein said support means comprises a plunger displaceable in a bore of said shank and a projection extending transversely of a longitudinal extent of said shank and projecting through a slot in the shank body to be engaged by a surgeon, said plunger having a front end portion and a nylon cord secured to said front end portion, extending in said bore and engaging said band means.

8. A surgical instrument for seating an intraocular lens in the posterior capsule of an eye, said instrument comprising:

a longitudinally extending hollow shank having a tip portion;

flexible band means forming a loop extending forwardly of said tip portion for embracing the intraocular lens;

said tip portion having a generally S-shape to allow said tip portion to curl around the iris of the eye to position said loop with the intraocular lens held therein inside the posterior capsule in a plane generally parallel to the posterior wall of the capsule; and support means connected to said band means and displaceable in said hollow shank relative thereto to provide for release of the lens by said loop to enable withdrawal of said band means from the eye without disturbing the seating of the intraocular lens in the posterior capsule of the eye.

9. A surgical instrument as set forth in claim 8 wherein said shank has a bore and a longitudinal slot intersecting said bore, and said support means comprises a plunger member displaceable in said bore and a projection extending from said plunger member transverse to the longitudinal axis of said plunger member and through said longitudinal slot for engagement by a surgeon, said band means being releasably connected with said plunger member.

10. A surgical instrument as set forth in claim 9 wherein said longitudinal slot has a front surface defining a forward position of said plunger member in said shank in which said loop is larger than the lens to be held therein, and said shank has a first transverse slot for receiving said projection and defining an intermediate position of said plunger member in said shank in which said loop is adapted to snugly hold the intraocular lens, and a second transverse slot located further away from said tip portion than said first slot for receiving said projection and defining a rearward position of said plunger member in said shank in which said band means releases the lens.

11. A method of inserting an intraocular lens into the posterior capsule of an eye with a surgical instrument for holding the intraocular lens and having a longitudinally extending hollow shank having a generally S-shaped tip portion, and band means attached to said shank and forming a loop extending forwardly of said tip portion for embracing the intraocular lens, said method comprising the steps of:

inserting the surgical instrument with the intraocular lens held in said loop through an incision made in the cornea of the eye and positioning said loop with the intraocular lens held therein inside the posterior capsule in a plane generally parallel to the posterior wall of the capsule, the S-shape of the tip portion allowing the shank to clear the iris of the eye when said loop is positioned in the plane generally parallel to the posterior wall of the capsule;

breaking the loop to release the lens and enable withdrawal of the band means from the eye without disturbing the seating of the lens in the posterior capsule of the eye; and thereafter, withdrawing the surgical instrument from the eye.

12. A surgical instrument for seating an intraocular lens in the posterior capsule of an eye and comprising:

a longitudinally extending hollow shank having a tip portion;

flexible band means forming a loop extending forwardly of said tip portion for embracing the intraocular lens, said shank tip portion having a generally S-shape to allow said tip portion to curl around the iris of the eye to position said loop with the intraocular lens held therein inside the posterior capsule in a plane generally parallel to the posterior wall of the capsule; and support means displaceable within said hollow shank and connected to said band means;

said displaceable support means having in said hollow shank a forward position in which said loop is larger than the lens to be held therein, and an intermediate position in which said loop snugly retains the lens, and a means associated with said bank means for severing the latter so as to release the lens and to enable withdrawal of said band means from the eye without disturbing the seating of the lens in the posterior capsule of the eye.

* * * * *